US009630008B2

(12) United States Patent
McLaughlin et al.

(10) Patent No.: US 9,630,008 B2
(45) Date of Patent: Apr. 25, 2017

(54) SINGLE CHANNEL COCHLEAR IMPLANT ARTIFACT ATTENUATION IN LATE AUDITORY EVOKED POTENTIALS

(71) Applicants: THE REGENTS OF THE UNIVERSITY OF CALIFORNIA, Oakland, CA (US); THE PROVOST, FELLOWS AND SCHOLARS OF THE COLLEGE OF THE HOLY AND UNDIVIDED TRINITY OF QUEEN ELIZABETH NEAR DUBLIN, Dublin (IE)

(72) Inventors: Myles McLaughlin, Aliso Viejo, CA (US); Alejandro Lopez Valdes, Dublin (IE); Richard Reilly, Dublin (IE); Fan-Gang Zeng, Irvine, CA (US)

(73) Assignees: THE REGENTS OF THE UNIVERSITY OF CALIFORNIA, Oakland, CA (US); THE PROVOST, FELLOWS AND SCHOLARS OF THE COLLEGE OF THE HOLY AND UNDIVIDED TRINITY OF QUEEN ELIZABETH NEAR DUBLIN, Dublin (IE)

( * ) Notice: Subject to any disclaimer, the term of this patent is extended or adjusted under 35 U.S.C. 154(b) by 0 days.

(21) Appl. No.: 14/773,182

(22) PCT Filed: Mar. 5, 2014

(86) PCT No.: PCT/US2014/020827
§ 371 (c)(1),
(2) Date: Sep. 4, 2015

(87) PCT Pub. No.: WO2014/138269
PCT Pub. Date: Sep. 12, 2014

(65) Prior Publication Data
US 2016/0008598 A1 Jan. 14, 2016

Related U.S. Application Data

(60) Provisional application No. 61/775,345, filed on Mar. 8, 2013.

(51) Int. Cl.
*A61N 1/00* (2006.01)
*A61N 1/36* (2006.01)
(Continued)

(52) U.S. Cl.
CPC ....... *A61N 1/36032* (2013.01); *A61N 1/0541* (2013.01); *A61N 1/3727* (2013.01); *H04R 25/507* (2013.01)

(58) Field of Classification Search
CPC .... A61N 1/04; A61N 1/04001; A61N 1/0402; A61N 1/0476; A61N 1/0488; A61B 5/36032
See application file for complete search history.

(56) References Cited

U.S. PATENT DOCUMENTS

| 6,157,861 A | 12/2000 | Faltys et al. |
| 6,181,961 B1 | 1/2001 | Prass |
| 6,771,067 B2 | 8/2004 | Kellman et al. |

OTHER PUBLICATIONS

PCT Search Report and Written Opinion for Application No. PCT/US2014/020827, dated Jun. 20, 2014.

*Primary Examiner* — Scott Getzow
(74) *Attorney, Agent, or Firm* — Knobbe Martens Olson & Bear LLP

(57) ABSTRACT

Disclosed herein are embodiments of methods and systems for attenuating artifacts in single channel cochlear implants. Both high and low frequency artifacts can be attenuating using embodiments of the disclosed methods and systems.

(Continued)

In some embodiments, low-pass filters, impedance balancing, and DC artifact estimation can be used, alone or in combination, to attenuate or completely remove artifacts in single channel cochlear implants.

18 Claims, 10 Drawing Sheets

(51) Int. Cl.
*A61N 1/05* (2006.01)
*A61N 1/372* (2006.01)
*H04R 25/00* (2006.01)

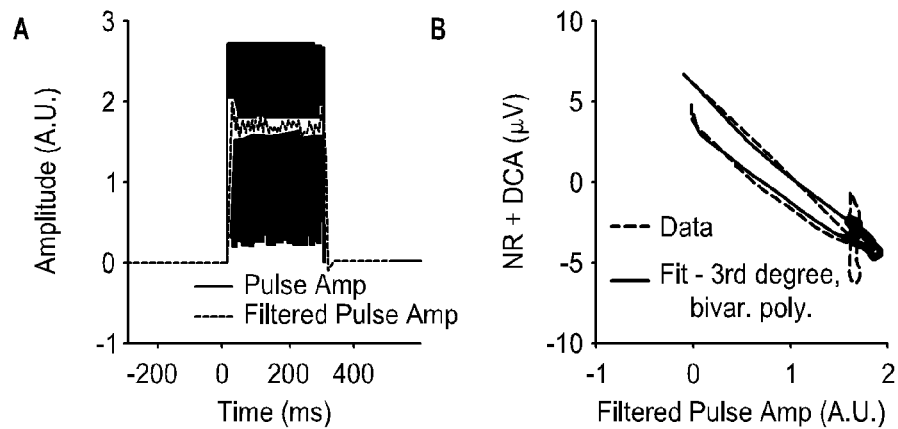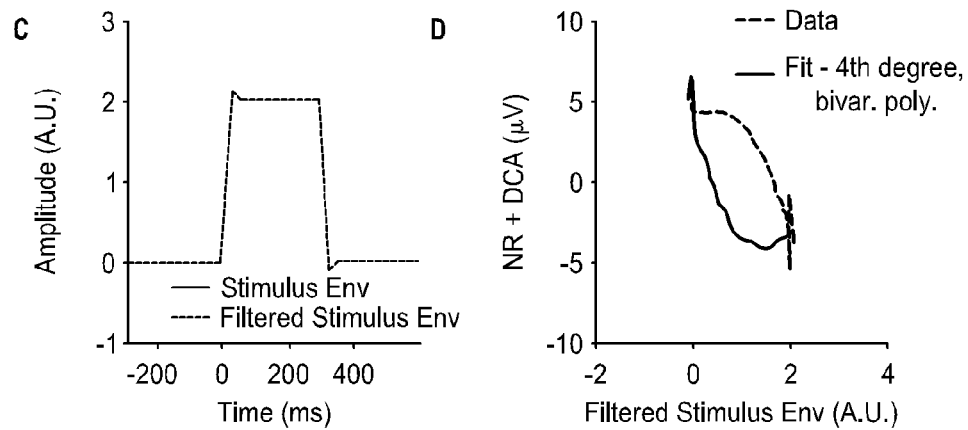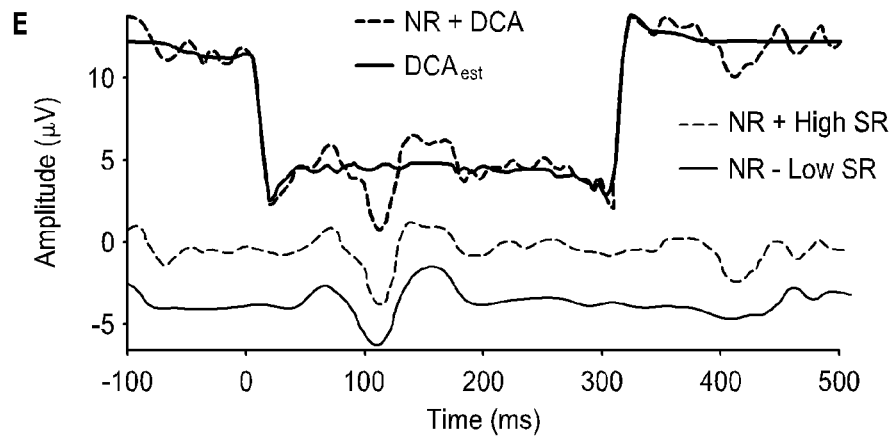
FIG. 5A-E

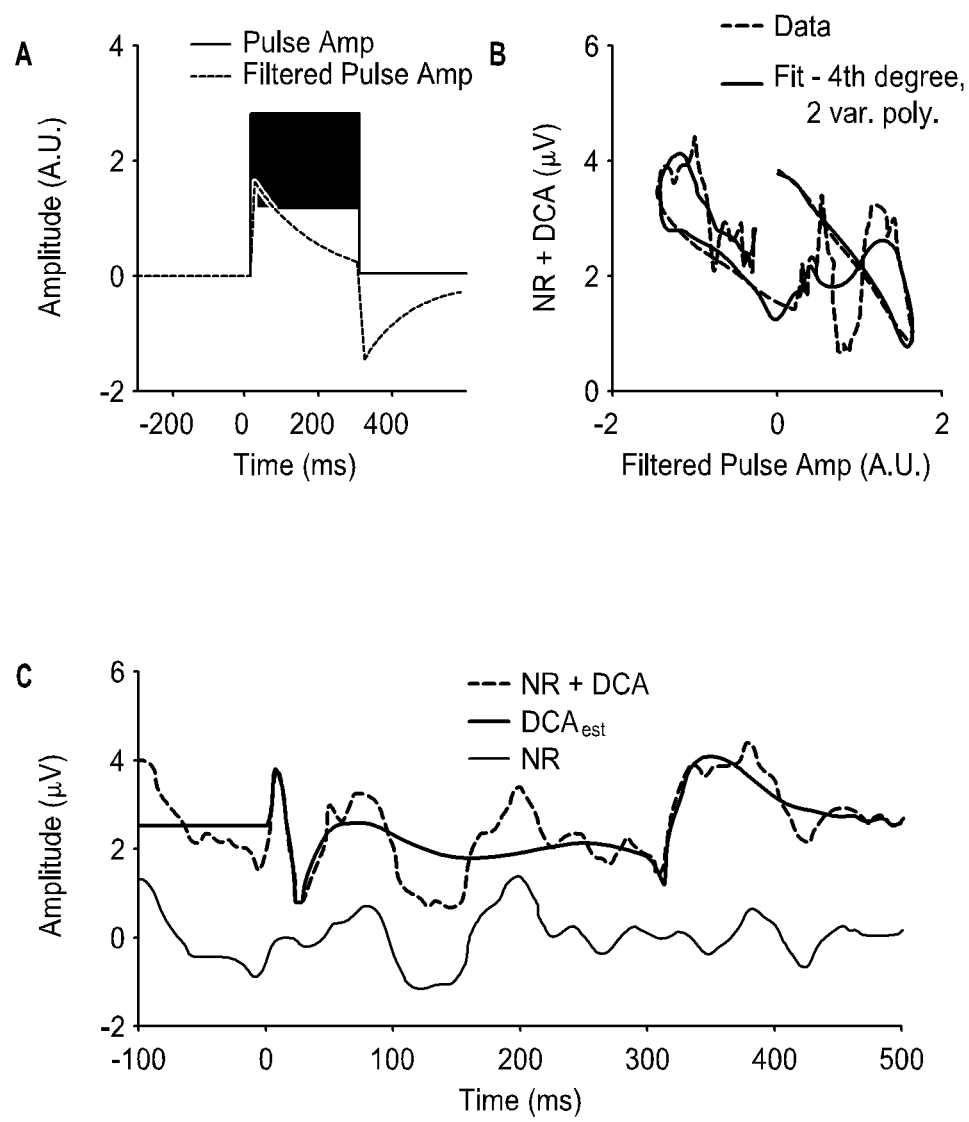
FIG. 6A-C

FIG. 8A-K

FIG. 9A-K

SINGLE CHANNEL COCHLEAR IMPLANT ARTIFACT ATTENUATION IN LATE AUDITORY EVOKED POTENTIALS

INCORPORATION BY REFERENCE TO ANY PRIORITY APPLICATIONS

This application claims priority from U.S. Provisional Patent Application No. 61/775,345, filed Mar. 8, 2013.

BACKGROUND

Field

This disclosure relates generally to the attenuation of single channel cochlear implant artifacts.

Description of the Related Art

Advances in cochlear implant (CI) technology now mean that a typical recipient of modern CI can expect to understand quiet speech in a listening environment. In spite of these advances, there remains a large amount of variability in an individual user's performance. Behavioral methods such as speech perception tests or non-speech based listening tests can be used to quantify this variability. However, behavioral methods are often not suitable for pediatric CI users. Further, speech-based tests may not be the best way to assess the performance of new CI recipients while they are still learning to understand speech heard through their implants. Neural based objective metrics of performance may provide a useful alternative to behavioral testing in both these user groups. In addition to potentially improving the standard of treatment received by an individual CI user, the development of neural objective metrics of CI performance may also advance understanding of the origins of the performance variability by giving information on the underlying neural mechanisms. However, the development of such neural metrics has been hampered by the large CI related electrical artifact which contaminates evoked potential recordings in these subjects.

SUMMARY

Disclosed herein are embodiments of a single channel artifact cancellation method, the method can comprise recording a single channel neural response signal from a patient using at least one electrode, wherein the neural response signal comprises at least one high frequency artifact, at least one low frequency artifact, and an attenuated neural response signal, attenuating the high frequency artifact by passing the recorded signal through a low-pass filter, and attenuating the low frequency artifact by balancing impedance in the at least one electrode, wherein, if the low frequency artifact remains after balancing impedance in the at least one electrode, further attenuating the low frequency artifact by estimating the low frequency artifact and subtracting the estimate from the recorded signal, and wherein the attenuated neural response signal is obtained after the attenuations.

In some embodiments, the attenuated neural response signal can be obtained by using the equation:

$$NR(t) \approx SIG_f(t) - DCA_{est}(t)$$

wherein t is time, NR(t) is the attenuated neural response signal, $SIG_f(t)$ is the recorded signal, and $DCA_{est}(t)$ is the estimated low frequency artifact.

In some embodiments, the artifacts can be completely removed after the method is performed.

In some embodiments, the neural response signal can be represented by the equation:

$$SIG(t) = NR(t) + HFA(t) + DCA(t)$$

wherein t is time, SIG(t) is the recorded signal, NR(t) is the attenuated neural response signal, HFA(t) is the high frequency artifact, and DCA(t) is the low frequency artifact.

In some embodiments, balancing impedance can comprise balancing impedances within 1 kΩ. In some embodiments, estimating the low frequency artifact can comprise using pulse amplitude.

In some embodiments, the low frequency artifact can be estimated by the equation:

$$DCA = f(PA, t)$$

wherein DCA is the low frequency artifact, PA is pulse amplitude and t is time.

In some embodiments, the low frequency artifact can be estimated by the equation:

$$DCA = \Sigma_{ij} a_{ij} PA^i t^j$$

wherein DCA is the low frequency artifact, PA is pulse amplitude, t is time, a is a coefficient for each term in the polynomial and i and j determine the degree of the polynomial.

In some embodiments, the polynomial can be a $3^{rd}$ degree polynomial. In some embodiments, estimating the low frequency artifact can comprise using a stimulus envelope.

Also disclosed herein are embodiments of a system for cancelling a single channel artifact, the system can comprise a recorder configured to record a single channel neural response signal from a patient using electrodes, wherein the neural response signal comprises at least one high frequency artifact, at least one low frequency artifact, and an attenuated neural response signal, a processor operably coupled to the recorder, wherein the process is configured to, attenuate the high frequency artifact by passing the recorded signal through a low-pass filter, and attenuate the low frequency artifact by balancing impedance in the electrodes, wherein, if the low frequency artifact remains after balancing impedance in the electrodes, the processor is further configured to attenuate the low frequency artifact by estimating the low frequency artifact and subtracting the estimate from the recorded signal; and an output device operably coupled to the processor, wherein the processor is configured to communicate the attenuated neural response signal with the artifacts attenuated to the output device.

In some embodiments, the output device can be selected from the group consisting of a monitor, printer, or speaker. In some embodiments, the processor can comprise a memory device. In some embodiments, the system can completely remove the artifacts.

In some embodiments, the processor can comprise a program to estimate the low frequency artifact using the equation:

$$DCA = f(PA, t)$$

wherein DCA is the low frequency artifact, PA is pulse amplitude and t is time.

In some embodiments, the processor can comprise a program to estimate the low frequency artifact using the equation:

$$DCA = \Sigma_{ij} a_{ij} PA^i t^j$$

wherein DCA is the low frequency artifact, PA is pulse amplitude, t is time, a is a coefficient for each term in the polynomial and i and j determine the degree of the polynomial.

In some embodiments, the recorder can record a signal selected from the group consisting of an electrocardiograph, electromyograph, magnetoencephalography, electronystagmograph, or electroencephalograph. In some embodiments, the processor can be configured to be the recorder.

BRIEF DESCRIPTION OF THE DRAWINGS

FIGS. 5A-E illustrate an embodiment of a method for DC artifact estimation from the pulse amplitude or stimulus envelope and removed.

FIGS. 6A-C illustrates the effect of the amplifier high-pass filter on the DC artifact in some embodiments.

DETAILED DESCRIPTION

Figure 1:
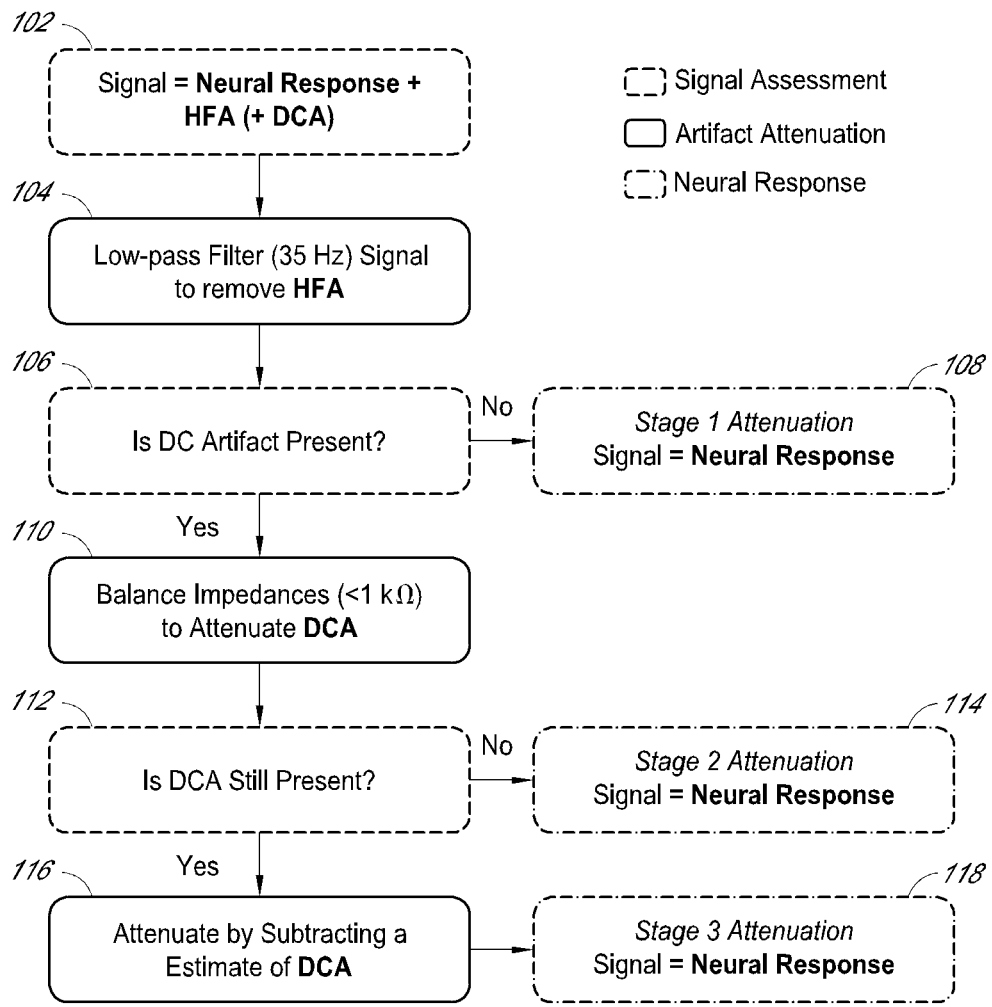
FIG. 1 illustrates a flow chart showing an embodiment of an artifact attenuation method disclosed herein.

The below disclosure discusses embodiments of methods and systems for attenuating artifacts out of single channel data cochlear implants (CIs) to analyze late auditory evoked potentials (LAEPs). Recent evidence suggests that LAEPs can provide a useful objective metric of performance in CI subjects. Cortical evoked potential may be useful at predicting speech perception outcomes in CI subjects, more so than earlier evoked potential responses such as auditory nerve electric compound action potentials (ECAPs) or auditory brainstem responses. However, the CI can produce a large electrical artifact that can contaminate LAEP recordings and can confound their interpretation.

In some embodiments, attenuation of artifacts can occur in a three stage, single channel, artifact attenuation approach which can allow for the recording of LAEPs in CI subjects. The disclosed attenuation approach can allow for accurate measurement of LAEPs in CI subjects from single channel recordings, increasing their feasibility and utility as an accessible objective measure of CI function. Further, embodiments of the single channel attenuation approach may facilitate research into LAEPs in CI users and could help develop a clinically applicable objective neural metric of CI performance. The disclosed method and system can be used with a wide range of complex stimuli including, but not limited to, tone complexes, amplitude modulated tones, or noise and spectral ripple stimuli.

The term "attenuate" as used herein has its ordinary meaning to persons having skill in the art. Attenuation can lead to the reduction, removal, cancellation, or destruction of artifacts and attenuation can include the complete removal, cancellation, or destruction of artifacts. In some embodiments, attenuation reduces artifacts to less than about 1%, 5%, 10%, 15%, 20%, or 30% of their original values. In some embodiments, successful attenuation of an artifact can be objectively determined. In some embodiments, successful attenuation of artifact can be judged by visual inspection of the LAEP, which can be a subjective assessment. However, three points provide reassurance that, after the single channel artifact attenuation procedure has been applied, the effect of any remaining artifact on the neural response can be negligible.

Single-Channel Approach

Cortical evoked potentials may be more useful at predicting speech perception outcome in CI users than auditory brainstem responses or auditory nerve compound action potentials. However, to minimize artifacts, very short, simple, stimuli are typically used which are unable to fully probe the complex processing that takes place in the auditory system. It can be advantageous to attenuate artifacts caused by longer duration stimuli. Independent component analysis (ICA) could be used to recover late auditory evoked potentials (LAEP) from multi-channel data. Utilizing the multi-channel ICA approach, LAEPs obtained using a mismatch negativity paradigm can provide useful information on CI functionality and that this information can be related to behavioral outcomes such as speech perception. One drawback of the ICA approach is that multi-channel data must be acquired, even when most of the results and conclusions are based on artifact free single channel data. Having to acquire multi-channel data requires necessitates the purchase of expensive multi-channel acquisition systems, increases subject preparation time as a full EEG cap must be attached and, in CI subjects, has the added difficulty of positioning the EEG cap over the behind-the-ear processor and magnetic link. For most clinical applications and many research questions single channel data is sufficient and subject preparation time much shorter. Further, the applicability of the ICA approach is limited when only single channel data are needed or available, as is often the case in both clinical and research settings. The ICA based approach is useful in a research setting but, because of the necessity for multi-channel data, it practical application in a clinical setting is limited.

Embodiments of the disclosed method are therefore advantageous as they attenuate the CI related artifacts from a single-channel approach, and eliminate the necessity for multi-channel data. Moreover, embodiments of the artifact attenuation approach outlined herein can facilitate the study of LAEPs in CI subjects by allowing researcher and clinicians to use single channel systems, thereby reducing subject preparation time and difficulties associated with placing the multi-channel cap over the CI. Accordingly, disclosed herein are embodiment of a single-channel, high sample rate (about 100, 105, 110, 115, 120, 125, 130, 135, 140, 145, or 150 kHz), and high bandwidth (about 0-100, or about 10-90, or about 20-80 kHz) acquisition system to attenuate and/or remove the CI stimulation artifact.

LAEPs can be measured in CI subjects by using the CI itself as a recording device, removing the need to attach scalp electrodes or have a dedicated LAEP acquisition system. Combining the LAEP CI recording technique with this single channel artifact cancellation approach could greatly increase the ease of access to LAEPs: just as an ECAP can be measured directly from the CI, so too could LAEPs. In a small population of CI users, a significant correlation between speech perception in quiet and a measure of mid-latency Na-Pa amplitude normalize for different stimulation levels. A mismatch negativity measure could discriminate between good and bad performers on a speech perception task. By eliminating the need for multi-channel recordings, thereby reducing recording times, embodiments of the disclosed single channel approach can facilitate the study of larger populations of CI subjects and may help in the development of an improved neural objective measure of CI performance. Behaviorally it has been shown that more complex stimuli which probe the spectral discrimination of CI user can be used to provide a reasonable estimate of speech perception. Combining this single channel artifact cancellation approach with a mismatch negativity paradigm using spectrally rippled stimuli can provide a clinically applicable objective neural estimate of a CI user's spectral resolution.

Accordingly, disclosed herein are embodiments of a high sample rate, high bandwidth single channel acquisition system with a temporal resolution high enough to clearly resolve each stimulation pulse. LAEPs recorded in CI subjects are generally composed of three components: a neural response component and two artifact components. The high frequency artifact (HFA) can be a direct representation of stimulation pulses and can be partially or completely attenuated by a low-pass filter (stage 1). As discussed in more detail below, high frequency artifact can be partially or completely attenuated by a 35 Hz low-pass filter. The low frequency or direct current (DC) artifact (DCA), often referred to as a 'pedestal' artifact, could be caused by an electrode impedance mismatch, and in some subjects could be attenuated by balancing the impedance of the recording electrodes (stage 2). In some embodiments, the DC artifact can be caused by an impedance mismatch, and thus can be removed when electrode impedances are balanced within 0.5, 1, 2, 3, 4, or 5 kΩ. However, if impedance balancing does not attenuate the DCA, a bivariate polynomial mathematical framework can be used to obtain an estimate of the DCA and remove it from the LAEP (stage 3). The DCA can show a non-linear time varying relationship to pulse amplitude, and can be well described by a bivariate polynomial. This single channel approach can also be applied with low sample rate data (commercial systems) and can be used to measure N1-P1 amplitude growth functions in CI users. The N1-P1 amplitude growth is measure as the first negative (N1) and first positive (P1) peak in cortical auditory evoked potentials.

Artifact Attenuation

Upon examination of LAEPs, it was found that recorded neural signals (SIG) can be made up of a neural response component (NR) and two artifact components, a high frequency artifact (HFA) and a low frequency artifact (DCA). Thus the recorded signal could be represented by the following equation, where t is time:

$$SIG(t) = NR(t) + HFA(t) + DCA(t) \qquad \text{Eq. 1}$$

It can be advantageous to remove the artifact components from SIG, thus leaving only the neural release component. Accordingly, embodiments of the disclosed three-stage, single channel, artifact attenuation method can be used to attenuate and or remove the artifacts so that only the neural release component remains. Each stage is explained in detail below and flow chart outlining the approach is shown in FIG. 1. In some embodiments, a recorded neural signal can be obtained 102. The signal can be, for example, obtained through the use of electrodes on a patient, though the method of recordation is not limiting. The signal can contain the neural response, as well as one or more artifacts (HFA, DCA, or a combination of both). In some embodiments, the HFA and DCA can be separately removed from the recorded signal.

In some embodiments, a low-pass filter signal can be used to remove the HFA 104. The low-pass filter signal is a filter that can pass low-frequency signals and attenuate signals with frequencies higher than a cutoff frequency. In some embodiments, either acoustic or electronic low-pass filter signals can be used. The low-pass filter signal can be, for example, about 1, 2, 5, 10, 15, 20, 25, 30, 35, 40, or 45 Hz, though the signal Hz is not limiting. The low-pass filter signal can remove greater than about 80%, greater than about 90%, greater than about 95%, greater than about 99%, or about 100% of the HFA from the recorded signal. After the HFA has been removed 104, the signal can be checked for the DCA 106. In some embodiments, the signal can be checked 106 visually. In some embodiments, a computer system can be used to check 106. If the DCA is not present, the signal is the neural response 108 and no further steps need to be taken.

If the DCA is still present, an impedance balance can be performed 110 to attenuate the DCA. In some embodiments, impedances could be balanced to within about 0.5, 1, 1.5, 2, 2.5, 3, 3.5, 4, 4.5, or 5 kΩ. In some embodiments, impedances could be balanced to within less than about 0.5, 1, 1.5, 2, 2.5, 3, 3.5, 4, 4.5, or 5 kΩ. The impedance balancing can remove greater than about 80%, greater than about 90%, greater than about 95%, greater than about 99%, or about 100% of the DCA. The method of balancing impedances is not limiting, and any type of impedance balancing method can be used. After impedances have been balanced 110, the signal can again be checked to see if the DCA is still present 112. If the DCA is not present, the signal is the neural response 114.

If the DCA is still present after impedance balancing, the signal can be further attenuating by subtracting an estimate of DCA 116. For example, in some embodiments setting the high-pass filter on the amplifier to DC or 0.03 Hz may give the clearest acquisition of the DCA and allow for the most straight forward application of the DCA estimation approach. As further described below, the DCA can be estimated from pulse amplitude or stimulus envelope, though other estimations can be used as well and are not limiting. In some embodiments, the estimation of the DCA can be greater than about 90%, greater than about 95%, greater than about 98%, greater than about 99%, or 100% of the actual DCA. The DCA estimation subtraction can remove greater than about 80%, greater than about 90%, greater than about 95%, greater than about 99%, or about 100% of the DCA from the recorded signal. Once the DCA estimate has been subtracted 116, the signal can be the neural response 118.

LAEP Study

Embodiments of the above-disclosed method were performed in a LAEP study. While some of the below disclosure is discussed relative to the study, the disclosure is not limited by the specifics of the study. LAEPs were measured in 22 adult CI subjects (7 male, 15 female) at two separate locations: Hearing and Speech Laboratory, University of California Irvine (n=7) and Trinity Centre for Bioengineering, Trinity College Dublin (n=15). Experimental procedures were approved by The University of California Irvine's Institutional Review Board and the Ethical Review Board at Trinity College Dublin. Informed consent was obtained from all subjects tested. Subjects were aged between 20 and 79 (mean 55.1, standard deviation 17.0) years old and used a device from one of the three main manufactures (Cochlear n=20, Advanced Bionics n=1, Med-El n=1).

Stimuli

Stimuli consisted of tone bursts at frequencies of either 250, 500 or 1000 Hz with durations of either 100, 300 or 500 ms. Broadband noise stimuli were also presented. Stimuli were presented at most comfortable level (MCL) and, when amplitude growth functions were collected, levels were decreased in equal decibel steps between MCL and threshold. Stimuli were generated in Matlab (Mathworks, Natick, Mass.) and presented either through a standard PC soundcard or DA converter (NI-USB 6221, National Instruments, Austin, Tex.) to the audio line-in on the subject's CI. Subjects used their everyday speech processing strategy without any special adjustments. This method of stimulation was chosen, as opposed to using a research interface to directly control the CI, because it represents a worst case scenario in terms of the CI artifact. It was reasoned that this would result in the development a robust artifact attenuation approach which could be easily applied in different settings and with different modes of stimulation.

Evoked Potential Recordings

To study the source of the CI related artifact in LAEP recordings a high temporal resolution EEG acquisition system was developed. It consisted of a high bandwidth, low noise, single channel differential amplifier (SRS 560, Stanford Research Systems, Sunnyvale, Calif.) connected to high sample rate AD converter (NI-USB 6221, National Instruments, Austin, Tex.). The sample rate on the AD converter was set to 125 kS/s, the low-pass filter on the amplifier was typically set to 100 kHz and the high-pass filter was set to either DC, 0.03 Hz, or 1 Hz. This system was designed to allow the CI related artifact to be clearly sampled with only minimal distortion being caused by the acquisition system. Custom software written in Matlab controlled the AD converter. The software performed online averaging and visualization of the LAEP and stored the raw data for offline analysis. Standard gold cup surface electrodes were used. An electrode placed at Cz was connected to the positive input on the amplifier, on the side opposite to the CI being tested an electrode placed on the mastoid was connected to the negative input on the amplifier and one placed on the collar bone was connected to the amplifier ground.

Attenuation of HFA with Low-Pass Filter

Figure 2:
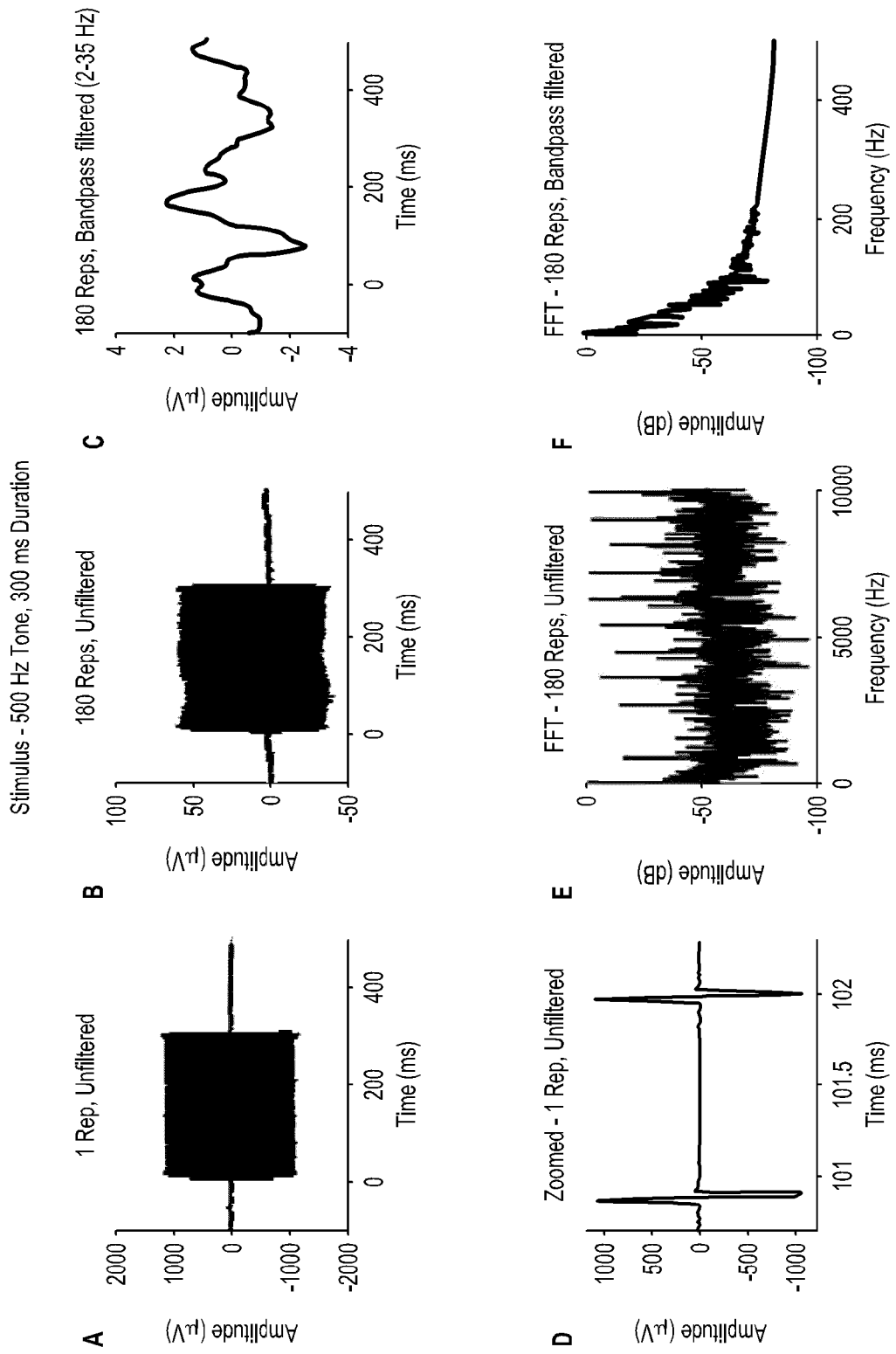
FIGS. 2A-F illustrates results of an embodiment of attenuation using a low-pass filter for removing a high frequency artifact.

FIGS. 2A-F illustrate an embodiment of a low-pass filter removing a high frequency artifact, which was generally in the mV range. All subjects in the study showed a HFA in their recorded signal. The high temporal resolution of the acquisition system can show that the HFA was caused by the CI stimulation pulses. As shown in FIG. 2A, the large amplitude high frequency artifact can be clearly visible after only one repetition. As shown in FIG. 2B, as the individual stimulation pulses do not sum in phase the high frequency artifact becomes smaller with more repetitions. Therefore, averaging together individual repetitions can cause a reduction in the HFA amplitude as the stimulation pulse in each repetition was not synchronized. The low frequency envelope can be caused by the neural response.

As shown in FIG. 2C, a band-pass (2-35 Hz) filter can attenuate the high frequency artifact to leave the neural response. FIG. 2C shows an LAEP collected in a CI subject after the HFA has been attenuated by filtering. The typical N1-P2 complex can be visible. As shown in FIG. 2D, zooming in on one repetition shows the individual stimulation pulses. The high temporal resolution of the acquisition system can show that the HFA was caused by the CI stimulation pulses As shown in FIG. 2E, the frequency spectrum of the unfiltered average data shows a strong component at that user's stimulation rate and harmonics of the stimulation rate. As shown in FIG. 2F, the HFA could be completely attenuated in all users with a 35 Hz low-pass software filter ($2^{nd}$ order Butterworth).

To examine how effective a hardware filter was at attenuating the HFA, LAEPs were collected in 3 subjects using a 30 Hz low-pass hardware filter on the amplifier (12 dB per octave). These were compared with LAEPs collected in the same subjects, during the same session, with a 100 kHz low-pass hardware filter and then subsequently digitally filter with a low-pass $2^{nd}$ order Butterworth filter. The type of low-pass filter is not limiting, and other types of low-pass filters could be used as well. The effect of attenuating the HFA using either a hardware or software filters was found to be similar.

Single, non-averaged, recordings of the response to one stimulus presentation showed that the HFA can be a direct representation of the stimulation pulses (see FIGS. 2A and D). In some embodiments, the HFA can be partially or completely attenuated by a low-pass filter (FIGS. 2C and F). In some embodiments, greater than about 90%, greater than about 95%, greater than about 99%, or about 100% of the HFA can be attenuated using a low-pass filter.

Most evoked potential studies in CI subjects use either a hardware or software low-pass filter at around 50 or 35 Hz. Although the majority of studies do not make a systematic investigation of it, this disclosure demonstrates that a low-pass filter can attenuate the HFA. A high sample rate system can be used to record auditory steady state responses in CI users. At low stimulation rates (40-80 pulses per second), the HFA could be removed by locating each stimulation pulse and linearly interpolating through it.

Attenuation of DCA with Impedance Balancing

Figure 3:
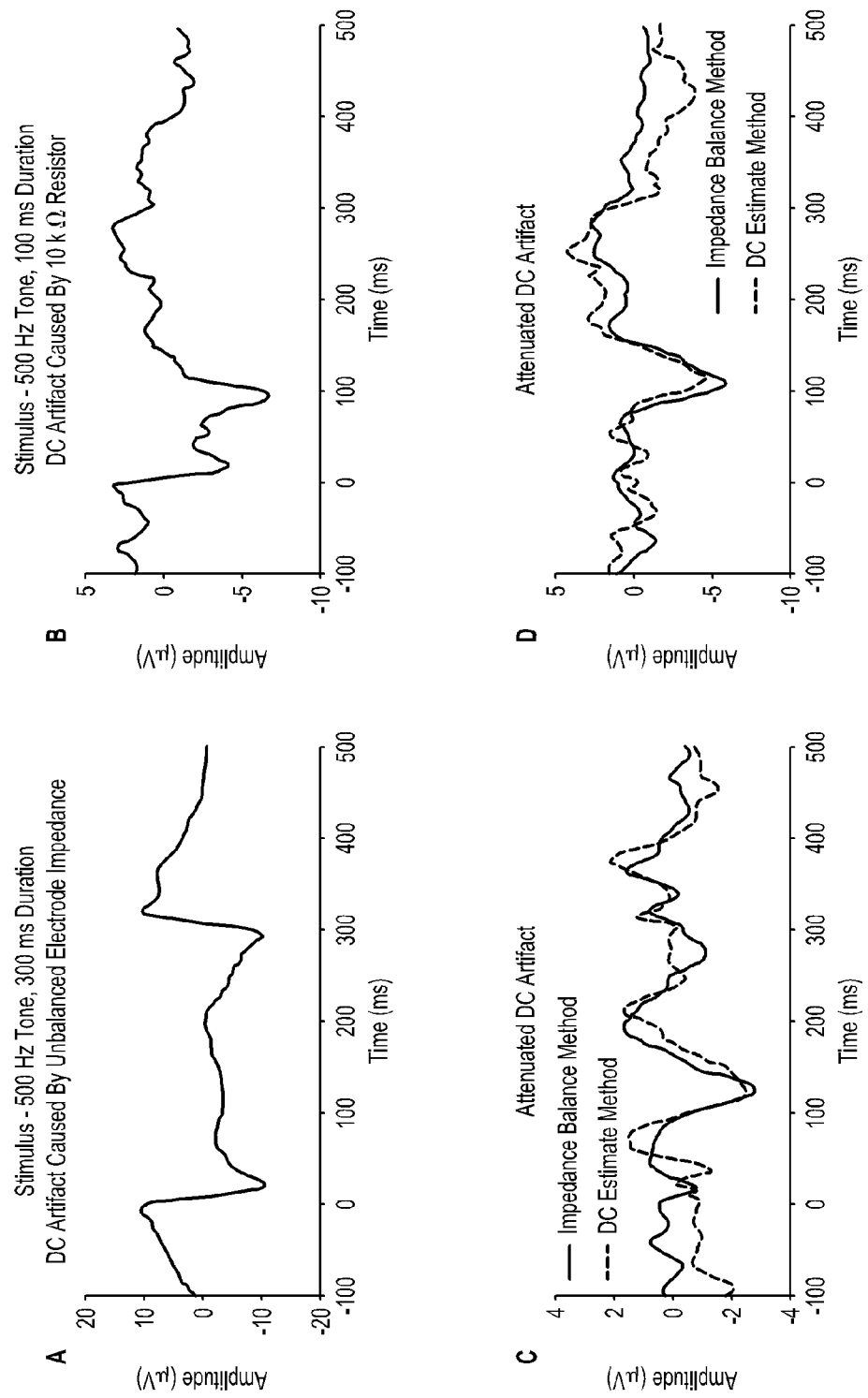
FIGS. 3A-D illustrate an embodiment of a method and results for removing a low frequency artifact caused by an impedance mismatch.

After removal of the HFA, a low frequency artifact (DCA) was observed in some subjects. In some embodiments, DCAs could be caused an impedance mismatch. FIG. 3 illustrates how a DCA can be caused by an impedance mismatch. FIG. 3A shows the DCA in a subject before impedance balancing and after low-pass filtering. In general, it was found that the size of the DCA was related to the size of the impedance mismatch between electrodes. Balancing electrode impedance reduced the size of the DCA and, in some cases, completely attenuated the DCA. For the LAEPs show in FIG. 3A, where a large DCA is apparent, electrode impedances were Cz=4.6 kΩ, Mastoid=2.9 kΩ and Ground=2.7 kΩ. Reducing the impedance on Cz to 2.6 kΩ completely attenuated the DCA (FIG. 3C, solid line). Applying a low-pass filter to remove the HFA and ensuring that electrode impedances were balanced to within 1 kΩ produced LAEPs which contained no visible artifacts in 27% (n=6) of subjects tested, thus no further attenuation would be needed. In the remaining 73% (n=16), even after impedance balancing, a DCA was present. In some embodiments, as shown in the study results, some subjects this DCA could be attenuated by ensuring that the electrode impedances were balanced to within 1 kΩ (FIG. 3C). In some embodiments, the high impedance electrode was removed, the skin prepared again and the electrode replaced.

To further examine the cause of the DCA, 3 subjects were selected who did not show a DCA. In these subjects, after the electrode impedances had been balanced, a DCA could be created by adding a 10 kΩ resistor between one of the electrode leads and the amplifier (FIG. 3B). After the resistor was removed the DCA was not present (FIG. 3D, solid line).

Attenuation of DCA by DCA Estimation

In some users the DCA may not be fully attenuated by impedance balancing procedure. In these subjects, embodiments of a DCA estimation method can be applied to further attenuate the artifact. In some embodiments, pulse amplitude (e.g., the amplitude of cochlear implant stimulation pulses measured here as artifact pulses) can be used to estimate and then attenuate the DCA. Where measurements of pulse amplitude are not available (as with standard low sample rate systems), the DCA could be estimated from a stimulus envelope. In some embodiments, an estimation from a stimulus envelope can be used instead of pulse amplitude. However, other DCA estimation procedures could be used as well, and the type of DCA estimation is not limiting.

Examination of the DCA showed that it can be related to the stimulation pulses, i.e. the onset and offset times of the DCA were similar to those of both the HFA and the stimulus, and the shape of the DCA was similar to that of the acoustic stimulus envelope (e.g. the slow time varying envelope of the acoustic stimulus) and the HFA envelope. Given these observation, it is reasonable to assume that the DCA can be described by a function of both stimulation pulse amplitude (PA) and time (t):

$$DCA = f(PA, t) \quad \text{Eq. 2}$$

Examination of the DCA in all subjects tested showed that this relationship was well approximated by a bivariate polynomial:

$$DCA = \Sigma_{ij} a_{ij} PA^i t^j \quad \text{Eq. 3}$$

where a is a coefficient for each term in the polynomial and i and j determine the degree of the polynomial.

Figure 4:
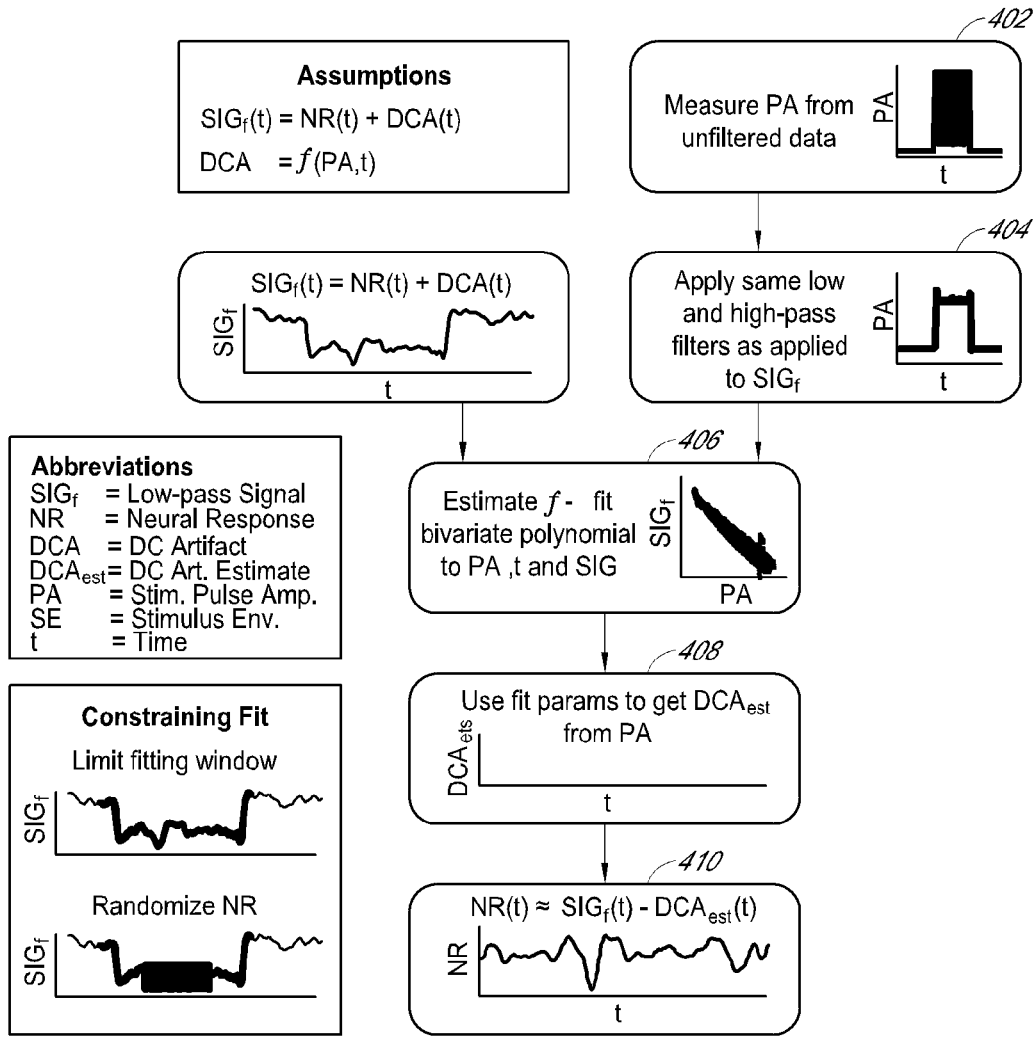
FIG. 4 illustrates a flow chart showing an embodiment of a method for DC artifact estimation from the stimulation pulse amplitude or stimulus envelope.

FIG. 4 illustrates a flow chart showing how the DC artifact can be estimated from the stimulation pulse amplitude (measurable with high sample rate acquisition systems) or stimulus envelope (for low sample rate systems) in some embodiments. The estimate of the DC artifact can be subtracted from the low-pass filtered signal to leave the neural response.

FIG. 4 shows how the polynomial coefficients were estimated from the recorded signal to give an estimate of the DCA. Firstly, pule amplitude (PA) was measured the unfiltered pulse-synchronized signal as a function time 402. PA in the averaged signal can become smaller because of unsynchronized pulses across stimulus repetitions (compare FIGS. 2A and B), i.e. stimulus onset and CI stimulation pulse generator are not synchronized. To create a pulse-synchronized averaged signal (only used to determine PA) a cross correlation between the first repetition and all other repetitions can be performed to determine the delay necessary for synchronization. Next, the averaged (non-synchronized) signal was low-pass filtered to remove the HFA 404, leaving just the NR and DCA:

$$SIG_f(t) = NR(t) + DCA(t) \quad \text{Eq. 4}$$

The same band-pass filter used on the signal (high-pass setting used on the amplifier and low-pass used in the software for HFA attenuation) can be applied to the PA time series. An estimate of the DCA can be obtained by fitting a bivariate polynomial 406 to these data using, for example, the polyfitn function in Matlab (available for download from the Mathworks File Exchange). However, other programs or methods for determining the bivariate polynomial can be used as well, and are not limiting. In the polynomial fitting function, the two independent variables were given as PA and t, and the dependent variable was $SIG_f$. The parameters obtained from the fitting function, i.e. the coefficients a, could then be in Eq. 3, together with the PA time series, to obtain an estimate of DCA ($DCA_{est}$) 408. To obtain the neural response, the DCA was attenuated by subtracting $DCA_{est}$ from $SIG_f$ 410:

$$NR(t) \approx SIG_f(t) - DCA_{est} \quad \text{Eq. 5}$$

To obtain a measure of PA, a high sample rate data can be used where the stimulation pulses are clearly resolved. Most commercially available acquisition systems cannot acquire data at these high sample rates. When a measure of PA is not available a measure of stimulus envelope (SE) can be substituted, as the SE is closely related to the PA.

The above described equations can allow an estimate of the DCA to be obtained from the recorded data and then attenuate the artifact by subtracting $DCA_{est}$ from the low-pass filtered signal (Eq. 5).

To test the effectiveness of the DCA estimation procedure it was applied to the waveforms shown in FIGS. 3A and B. The LAEP obtained using the DCA estimation procedure (FIGS. 3C and D, dashed lines), further described below, shows good agreement with the LAEP obtained using the impedance balancing method. Secondly, N1-P2 amplitudes and N1 latencies obtained at MCL are comparable to those reported in other studies. One study used the multi-channel ICA approach to measure LAEPs in 18 CI subjects. They reported a mean N1-P2 amplitude of 8.9 (±4.1 standard deviation) μV and mean N1 latency of 132.3 (±13.7 standard deviation) ms. Viola, F. C., Thorne, J. D., Bleeck, S., Eyles, J., & Debener, S. (2011) "Uncovering auditory evoked potentials from cochlear implant users with independent component analysis." *Psychophysiology*, 1-11. The study is hereby incorporated by reference in its entirety.

As shown in FIG. 3B, placing a 10 kΩ resistor between the Cz electrode and the amplifier also caused a DC artifact. As shown in FIG. 3C, balancing the electrode impedances (Cz=2.6, Mastoid=2.6, Ground=2.3 kΩ) attenuated the DC artifact (solid line). Applying the DC estimation method to the unbalanced data shown in FIG. 3A achieved a similar result (dashed line). As shown in FIG. 3D, removing the resistor completely attenuated the DC artifact (solid line). Applying the DC estimation method to the unbalanced data shown in FIG. 3B achieved a similar result (dashed line).

The cases where the DCA artifact was present and could be removed by impedance balancing (compare FIGS. 3A and C) or where the DCA was created by adding a resistor (FIG. 3B) provided a useful method by which to validate the DCA estimation approach described below. The dashed lines on FIGS. 3C and D show the LAEP obtained after applying the DCA estimation approach to the LAEP shown in FIGS. 3A and B respectively. The solid and dashed lines on FIGS. 3C and D show good agreement in shape and peak timing, indicating that DCA artifact estimation approach attenuated the artifact just as effectively as the impedance balancing method.

FIG. 5 illustrates how a DC artifact can be estimated from the pulse amplitude or stimulus envelope and removed in some embodiments. FIG. 5 shows an example of the different stages in the DCA estimation approach and compares the LAEPs obtained using both the PA and SE method.

FIG. 5A shows the PA measured as the difference between the minimum and maximum values of each pulse in the unfiltered signal (solid line). The same band-pass filter used to on the signal (high-pass from the amplifier and low-pass used in software to remove the HFA) was the applied to the PA (FIG. 5A, dashed line). As shown in FIG. 5A, stimulation pulse amplitude as a function of time (solid line) can be measured from the high sample rate signal. The same filter that was applied to the signal (band-pass 0.03-35 Hz) can be applied to the pulse amplitude measurement (dashed line).

As shown in FIG. 5B, plotting the low-pass filtered signal (NR+DCA) against pulse amplitude (dashed line) showed the complex, time varying, relationship between the two variables. A $3^{rd}$ degree bivariate polynomial was then fit to this data (i.e. PA, t, and NR+DCA). There is good agreement between the fitted polynomial function (FIG. 5B, solid line) and the data (dashed line). In some embodiments, $1^{st}$, $2^{nd}$, $3^{rd}$, $4^{th}$, $5^{th}$, $6^{th}$, $7^{th}$ $8^{th}$, $9^{th}$, or $10^{th}$ degree bivariate polynomials can be used, and the polynomial degree is not limiting.

As shown in FIG. 5C, with lower sample rate data where a measure of pulse amplitude cannot be obtained, a measurement of stimulus envelope (solid line) could be used instead. The same filter that was applied to the signal was applied to the stimulus envelope measurement (dashed line).

As shown in FIG. 5D, plotting the low-pass filtered signal (NR+DCA) against stimulus envelope (dashed line) showed the complex, time varying, relationship between the two variables. With these acquisition settings, the relationship was well described by a $4^{th}$ degree bivariate polynomial, the extra degree help to account for nonlinearities in the relationship between stimulus envelope and pulse amplitude.

The coefficients estimated from the fit were then used in Eq. 3 to obtain an estimate of the DCA from the PA (FIG. 5E, $DCA_{est}$ dashed line). The NR+high SR dashed line on FIG. 5E shows the NR, where the DCA has been attenuated by subtracting the $DCA_{est}$ (solid line) from NR+DCA (dashed line). As shown in FIG. 5E, the fit parameters could then be used to obtain an estimate of the DC artifact ($DCA_{est}$, solid line) from the pulse amplitude time sequence. The estimate of DC artifact from the stimulus envelope is not shown. Subtracting $DCA_{est}$ artifact from the low-pass filtered signal (NR+DCA, dashed line) leaves the NR. The NR+high SR dashed line shows the NR obtained from the pulse amplitude approach and the NR–low SR solid line shows the NR obtained from the high stimulus envelope approach. As shown both the NR+high SR and NR–low SR lines have a generally similar shape that can approximate the DCA.

In general, it was found that if the high-pass filter on the amplifier was set to DC or 0.03 Hz and the PA method was used, then the data (PA, t and NR+DCA) were well fit by a $3^{rd}$ degree polynomial. When high-pass filter on the amplifier was set DC or 0.03 Hz and the SE method was used the data were best fit with a $4^{th}$ degree polynomial (FIGS. 5C, D and E), the extra degree here accounting for the non-linear transformation between SE and PA.

With most commercial acquisition systems it is not possible to acquire data at a sample rate high enough to resolve individual stimulation pulses, making it difficult to obtain the measurement of PA shown in FIG. 5A. To accommodate data acquired with low sample rate systems, in some embodiments a stimulus envelope (SE) in place of the PA can be used to obtain an estimate of the DCA. To directly compare both methods the data shown in FIG. 5 were downsampled to 1250 S/s, simulating data acquired with a commercial acquisition system. The SE was obtained by rectifying and low-pass filtering (35 Hz, $2^{nd}$ order Butterworth) the stimulus. As with the PA the same band-pass filter applied to the signal (high-pass from the amplifier and low-pass from the software) was the applied to the SE. The dashed line on FIG. 5C shows the band-pass filtered SE, which in this case is almost identical to the SE (solid line, not visible) because the amplifier high-pass filter is close to DC (0.03) and it effect is negligible. However, when the high-pass filter is further from DC its effects become more significant (see FIG. 6) making it important to include this step. The dashed line of FIG. 5D shows the downsampled filtered signal (NR+DCA) plotted against the SE. Here, the data (SE, t, and NR+DCA) was well fit by a $4^{th}$ degree bivariate polynomial (FIG. 5D, solid line). In Eq. 3, PA was substituted with SE and the coefficients determined from the fit were then used to obtain an estimate of DCA from SE and t. The NR, obtained by subtracting the $DCA_{est}$ from the downsampled NR+DCA, is shown as the NR–low SR solid line on FIG. 5E (offset from zero). The high sample rate NR (NR–high SR dashed line) were the DCA has been attenuated using the PA method compares well with the low sample rate NR (NR–low SR solid line). No specific equation can be used for the stimulus envelope, as the equation will change dependent on what stimulus is used.

As mentioned above, 73% of subjects tested in the study resulted in DCA which could not be removed by impedance balancing. However, in all these subjects the DCA could be removed using the DCA estimation approach described above.

FIG. 6 illustrates the effect of the amplifier high-pass filter on the DC artifact in some embodiments. As shown in FIG. 6A, stimulation pulse amplitude as a function of time (solid line) can be measured from the high sample rate signal. The same filter that was applied to the signal (band-pass 1-35 Hz) was applied to the pulse amplitude measurement (dashed line). As shown in FIG. 6B, as the signal has been filtered it contains only neural response (NR) and DC artifact. Plotting the low-pass filtered signal against pulse amplitude against amplitude (Data, dashed line) shows the complex, time varying, relationship between the two variables. Due to the 1 Hz high pass filter, the relationship is best described by a $4^{th}$ degree polynomial (Fit, solid line), were time and pulse amplitude are the independent variables and the signal (NR+DCA) the dependent variable. As shown in FIG. 6C, the fit parameters are then used to obtain an estimate of the DC artifact ($DCA_{est}$, thick solid line) from the pulse amplitude time sequence. Subtracting $DCA_{est}$ from the low-pass filtered signal (NR+DCA, dashed line) leaves the NR (thin solid line).

When the high-pass filter was set to 1 Hz it produced a non-linear distortion of the DCA (FIG. 6), i.e. the DCA became smeared out in time. Data acquired with these settings were best fit by a $4^{th}$ degree polynomial (FIGS. 6A and B).

Polynomial Degree

The degree of a polynomial term used for estimating the DCA can be determined by, for example, the sum of the exponents, and the overall degree of the polynomial can be defined as the degree of the largest term. Thus, a bivariate $3^{rd}$ degree polynomial will contain a $PA^2$ t and a $PAt^2$ term but not a $PA^3t$ term. The degree of the polynomial which gives the best fit to that data can be related to the number of non-linear transformations between the PA or SE and the recorded signal. Different acquisition system settings can have different effects which influence these transformations and suggest the appropriate polynomial degree to be used in each case.

In some embodiments, when available (i.e. with high sample rate systems), using a measure of PA to estimate and then attenuate the DCA can be advantageous. When the amplifier high-pass filter is at DC or 0.03 Hz, the data (PA, t and NR+DCA) can be best fit with a $3^{rd}$ degree bivariate polynomial. If a measure of PA is not available (i.e. low sample rate systems) a measure of SE can be substituted and the bivariate polynomial degree may be increased by one to account for the extra non-linear transformation between PA and SE. If the data was acquired with the amplifier high-pass filter at 1 Hz, the bivariate polynomial degree may be increased by 1 to account for the non-linear effects of the filter.

Constraining the Fit

Eq. 3 shows the approximated relationship between DCA, PA and t. PA and t are known but the coefficients a and DCA are unknown. As described above, to estimate the coefficients, a bivariate polynomial was fit to PA, t and $SIG_f$, where $SIG_f$ contains both DCA and NR (see Eq. 4). In some embodiments, the most accurate estimate of DCA can be obtained when the fitting algorithm fits only to the DCA component of $SIG_f$ and not the NR component. A number of factors help constrain the fit to the DCA component only: 1) The PA (or SE) time series has a similar shape to the DCA. If the estimation procedure is conceptualized as transforming this PA time series into the $DCA_{est}$ then degree of the polynomial can determine how non-linear this transformation will be. Thus, a polynomial degree can be selected which was high enough allow this transformation but low enough to limit any fitting to the neural response. 2) Only a limited time window of the epoch, were the DCA is expected to occur, was used in the fitting procedure (see FIG. 4 'Constraining Fit' inset). This time window was determined by stimulus duration and the amplifier low-pass filter setting. If the amplifier low-pass filter was set to DC or 0.03 Hz, then the DCA was limited to the stimulus duration and only this portion of epoch was used in the fitting procedure (thick line on upper plot in inset). A low-pass filter setting of 1 Hz can cause the DCA to be smeared out in time and here a time window from stimulus onset to epoch end was used in the fitting procedure. 3) During a time window when it was expected that the DCA would be flat, i.e. 30 ms after stimulus onset and 30 ms before stimulus offset the order of elements in the $SIG_f$ vector were randomized (see FIG. 4 'Constraining Fit' inset, lower plot). The randomization procedure can preserve the statistical details of the $SIG_f$ during this time window (i.e. mean and standard deviation are unchanged) but removes temporal features of the NR, thus constraining the fitting procedure to the DCA component.

Amplitude Growth Functions

Figure 7:
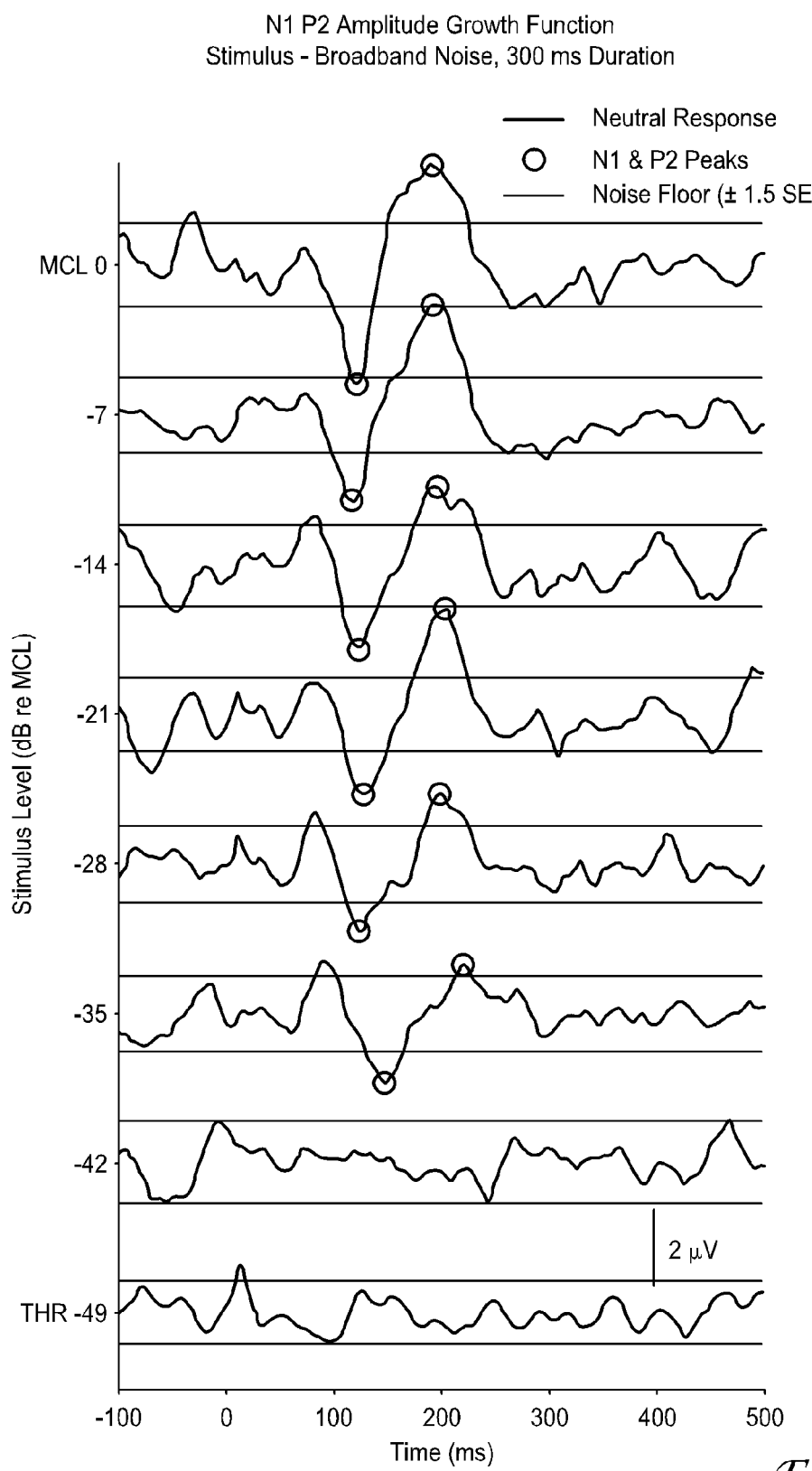
FIG. 7 illustrates a LAEP amplitude growth function in some embodiments. LAEPs (bold lines) were obtained at 8 levels, equally space on a dB scale from most comfortable level (MCL) to threshold (THR). N1 and P2 peaks were extracted (open circles). The latency of the N1 peak was only considered significant if was above the noise floor (light line).

In the study, the single channel, three stage artifact attenuation successfully attenuated both the HFA and the DCA in all subjects tested. Out of the 22 subjects tested, 20 showed the typical N1-P2 complex in the LAEP. Two subjects did not show any significant peaks in the LAEP. To test the robustness of the approach N1-P2 amplitude growth function were collected in the 6 of the 7 subjects tested at UC Irvine. FIG. 7 shows the LAEP waveforms (bold lines) collected in one subject at MCL and at 7 other level spaced in equal decibel steps down to threshold. The N1 peak was defined as the minimum peak in the LAEP between 50 and 200 ms and the P2 as the maximum peak occurring within 150 ms after N1. N1 and P2 are marked with blue circles on FIG. 7. To calculate a noise floor for each LAEP, the standard error for each time point in a long epoch (300 ms pre-stimulus to 800 ms post-stimulus) was calculated from the un-averaged, artifact attenuated, data. The noise floor (FIG. 7, light lines) was define as ±1.5 times the mean standard error across all time points in the long epoch.

Figure 8:
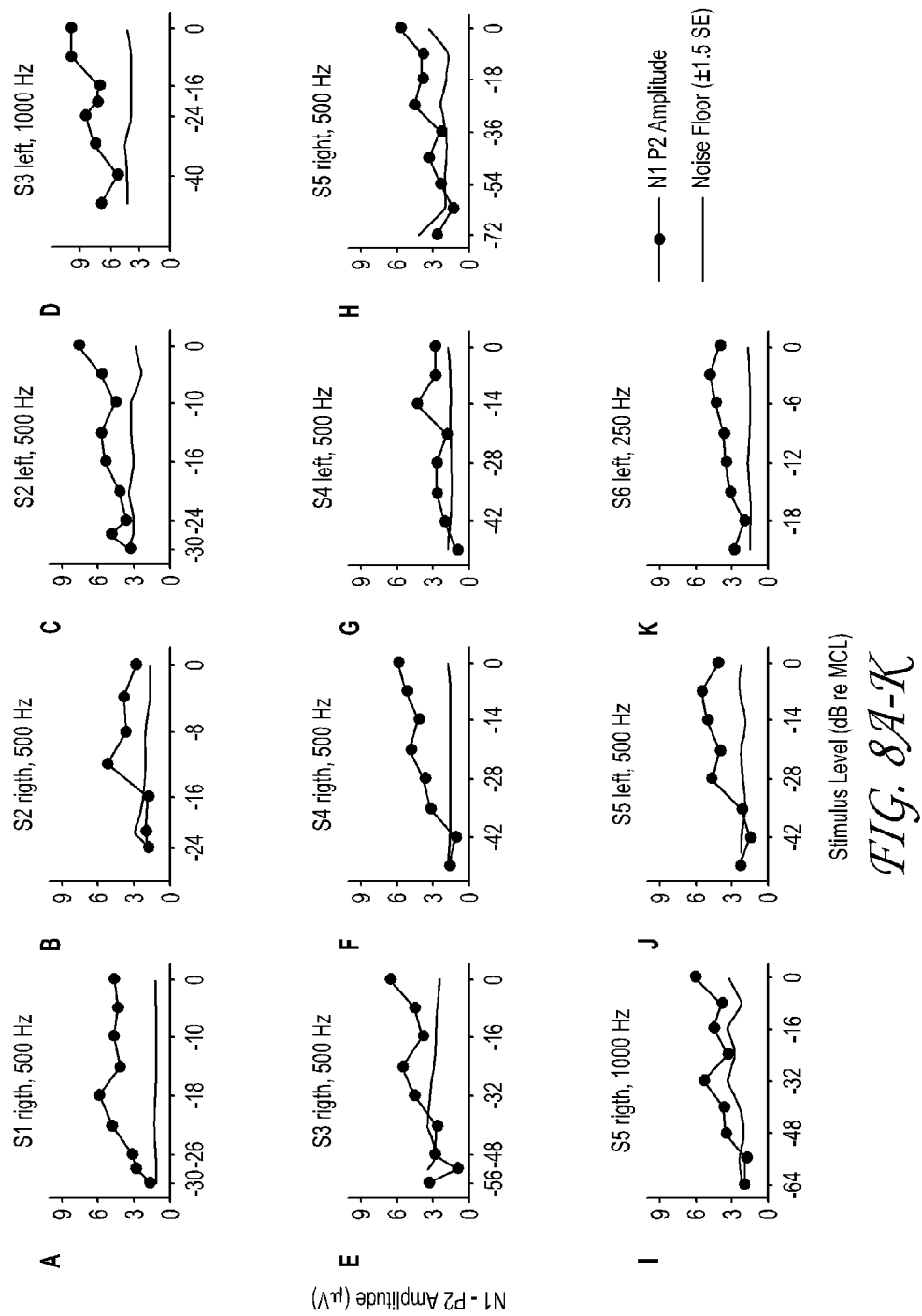
FIGS. 8A-K illustrate N1-P2 amplitude growth functions in some embodiments.
Figure 9:
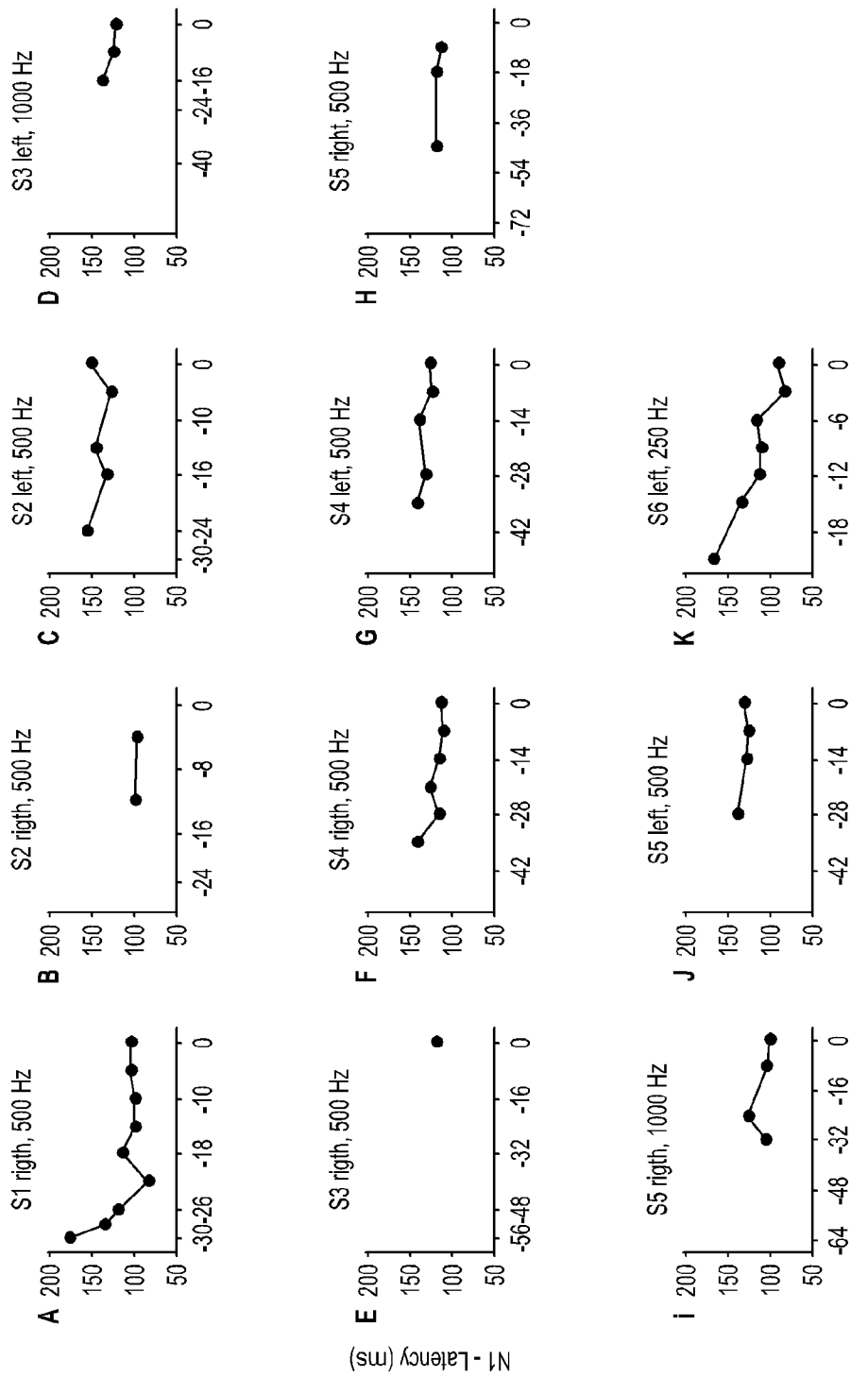
FIGS. 9A-K illustrates N1 latency functions for some embodiments.

FIGS. 8A-K and 9A-K show amplitude and latency metrics extract from 11 N1-P2 amplitude growth functions measured in 10 different ears in 6 subjects. The stimuli were 300 ms duration tones of 250, 500 or 1000 Hz. The difference in amplitude between the N1 and P2 peaks is shown as a function of stimulus level in FIG. 8. Some N1-P2 amplitude growth functions have a linear shape (e.g. FIG. 8F) while other show a plateau beyond a certain level (e.g. FIG. 8A). The shape was not always consistent between ears in the same subject (compare FIGS. 8B and C). Note the these amplitude growth function were collect by stimulating through the user's clinical processor and so include the effects of the compression function used in the speech processing strategy. FIG. 9 shows the latency of the N1 peak which either remained constant or showed an increase with decreasing level in all subjects. Only latencies of where the N1 peak amplitude was below the noise floor are shown. It was found that using the noise floor criteria, as defined above, objectively eliminated spurious N1 latency values at lower stimulation levels when the N1 peak amplitude became smaller. In all 20 subjects, when stimulated at MCL, the mean N1-P2 amplitude was 5.37 (SD=2.07) µV and mean N1 latency was 111.44 (SD=19.36) ms. The amplitude growth function (FIGS. 7, 8 and 9) show that N1-P2 amplitudes decrease and N1 latencies increase with decreasing level, as has been previously reported in normal hearing subjects.

System

Figure 10:
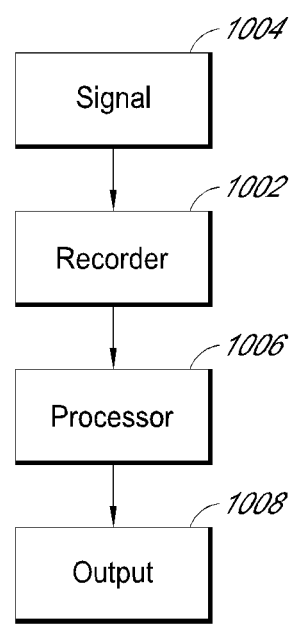
FIG. 10 illustrates an embodiment of a system for attenuating artifacts.

In some embodiments, as shown in FIG. 10, a system can be used to attenuate artifacts from a single channel neural response signal. For example, a recorder 1002 can be used to measure the single channel signal 1004 from a patient. This recorder 1002 can be, for example, a device for recording electrical signals from a patient, such as electrocardiography, electromyography, magnetoencephalography, electronystagmography, or electroencephalography. However, the method and device for recording the signal is not limiting.

In some embodiments, the recorder 1002 can be connected to a processor 1006, such as a computer processor. However, the type of processor is not limiting. This processor 1006 can be configured to attenuate the recorded signal 1004 using at least the above disclosed method. In some embodiments, the processor 1006 can output an attenuated signal to an output device 1008. In some embodiments, the processor 1006 can output, for example, a graph or chart showing the attenuated signal to an output device 1008. In some embodiments, an output device such as a monitor, printer, audio output, or speaker can be used. The type of output device is not limiting, and any desired output could be used.

Certain features that are described in this disclosure in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations, one or more features from a claimed combination can, in some cases, be excised from the combination, and the combination may be claimed as any subcombination or variation of any subcombination.

Moreover, while methods may be depicted in the drawings or described in the specification in a particular order, such methods need not be performed in the particular order shown or in sequential order, and that all methods need not be performed, to achieve desirable results. Other methods that are not depicted or described can be incorporated in the example methods and processes. For example, one or more additional methods can be performed before, after, simultaneously, or between any of the described methods. Further, the methods may be rearranged or reordered in other implementations. Also, the separation of various system components in the implementations described above should not be understood as requiring such separation in all implementations, and it should be understood that the described components and systems can generally be integrated together in a single product or packaged into multiple products. Additionally, other implementations are within the scope of this disclosure.

Conditional language, such as "can," "could," "might," or "may," unless specifically stated otherwise, or otherwise understood within the context as used, is generally intended to convey that certain embodiments include or do not include certain features, elements, and/or steps. Thus, such conditional language is not generally intended to imply that features, elements, and/or steps are in any way required for one or more embodiments.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than or equal to 10% of, within less than or equal to 5% of, within less than or equal to 1% of, within less than or equal to 0.1% of, and within less than or equal to 0.01% of the stated amount.

While a number of embodiments and variations thereof have been described in detail, other modifications and methods for the same will be apparent to those of skill in the art. Accordingly, it should be understood that various applications, modifications, materials, and substitutions can be made of equivalents without departing from the unique and novel disclosure or the scope of the claims.

What is claimed is:

1. A single channel artifact cancellation method, the method comprising:
    recording a single channel neural response signal from a patient using at least one electrode, wherein the neural response signal comprises at least one high frequency artifact, at least one low frequency artifact, and an attenuated neural response signal;
    attenuating the high frequency artifact by passing the recorded signal through a low-pass filter; and
    attenuating the low frequency artifact by balancing impedance in the at least one electrode;
    wherein, if the low frequency artifact remains after balancing impedance in the at least one electrode, further attenuating the low frequency artifact by estimating the low frequency artifact and subtracting the estimate from the recorded signal;
    wherein the attenuated neural response signal is obtained after the attenuations; and
    wherein the high frequency artifact is an artifact configured to be completely attenuated with a 35 Hz low-pass filter and the low frequency artifact is an artifact that remains after the high frequency artifact is attenuated by the 35 Hz low-pass filter.

2. The method of claim 1, wherein the attenuated neural response signal is obtained by using the equation:

$$NR(t) \approx SIG_f(t) - DCA_{est}(t)$$

wherein t is time, NR(t) is the attenuated neural response signal, $SIG_f(t)$ is the recorded signal, and $DCA_{est}(t)$ is the estimated low frequency artifact.

3. The method of claim 1, wherein the artifacts are completely removed after the method is performed.

4. The method of claim 1, wherein the neural response signal is represented by the equation:

$$SIG(t) = NR(t) + HFA(t) + DCA(t)$$

wherein t is time, SIG(t) is the recorded signal, NR(t) is the attenuated neural response signal, HFA(t) is the high frequency artifact, and DCA(t) is the low frequency artifact.

5. The method of claim 1, wherein balancing impedance comprises balancing impedances within 1 k$\Omega$.

6. The method of claim 1, wherein estimating the low frequency artifact comprises using pulse amplitude.

7. The method of claim 6, wherein the low frequency artifact is estimated by the equation:

$$DCA = f(PA, t)$$

wherein DCA is the low frequency artifact, PA is pulse amplitude and t is time.

8. The method of claim 7, wherein the low frequency artifact is estimated by the equation:

$$DCA = \Sigma_{ij} a_{ij} PA^i t^j$$

wherein DCA is the low frequency artifact, PA is pulse amplitude, t is time, a is a coefficient for each term in the polynomial and i and j determine the degree of the polynomial.

9. The method of claim 8, wherein the polynomial is a $3^{rd}$ degree polynomial.

10. The method of claim 1, wherein estimating the low frequency artifact comprises using a stimulus envelope.

11. A system for cancelling a single channel artifact, the system comprising:
    a recorder configured to record a single channel neural response signal from a patient using electrodes, wherein the neural response signal comprises at least one high frequency artifact, at least one low frequency artifact, and an attenuated neural response signal;
    a processor operably coupled to the recorder, wherein the process is configured to:
        attenuate the high frequency artifact by passing the recorded signal through a low-pass filter; and
        attenuate the low frequency artifact by balancing impedance in the electrodes;
        wherein, if the low frequency artifact remains after balancing impedance in the electrodes, the processor is further configured to attenuate the low frequency artifact by estimating the low frequency artifact and subtracting the estimate from the recorded signal;
    an output device operably coupled to the processor, wherein the processor is configured to communicate the attenuated neural response signal with the artifacts attenuated to the output device; and
    wherein the high frequency artifact is an artifact configured to be completely attenuated with a 35 Hz low-pass filter and the low frequency artifact is an artifact that remains after the high frequency artifact is attenuated by the 35 Hz low-pass filter.

12. The system of claim 11, wherein the output device is selected from the group consisting of a monitor, printer, or speaker.

13. The system of claim 11, wherein the processor comprises a memory device.

14. The system of claim 11, wherein the system completely removes the artifacts.

15. The system of claim 11, wherein the processor comprises a program to estimate the low frequency artifact using the equation:

$$DCA=f(PA,t)$$

wherein DCA is the low frequency artifact, PA is pulse amplitude and t is time.

16. The system of claim 15, wherein the processor comprises a program to estimate the low frequency artifact using the equation:

$$DCA=\Sigma_{ij}a_{ij}PA^i t^j$$

wherein DCA is the low frequency artifact, PA is pulse amplitude, t is time, a is a coefficient for each term in the polynomial and i and j determine the degree of the polynomial.

17. The system of claim 11, wherein the recorder records a signal selected from the group consisting of an electrocardiograph, electromyograph, magnetoencephalography, electronystagmograph, or electroencephalograph.

18. The system of claim 11, wherein the processor is configured to be the recorder.

* * * * *